Figure 1:
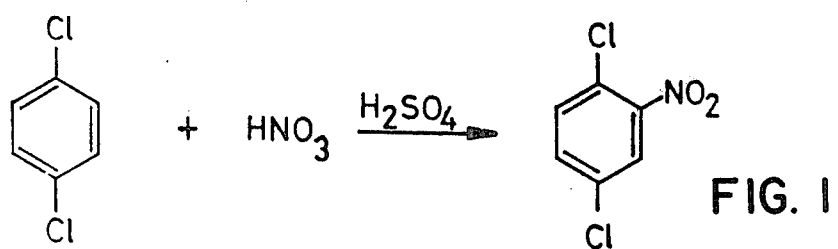
Figure 2:
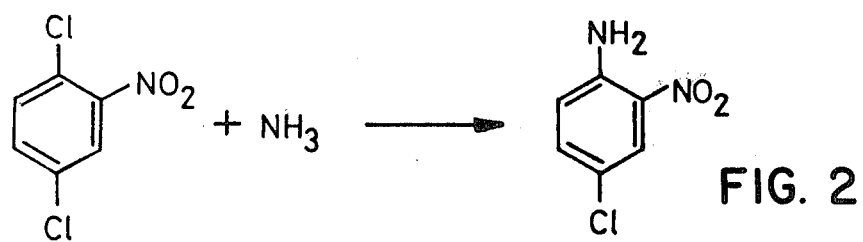
Figure 3:
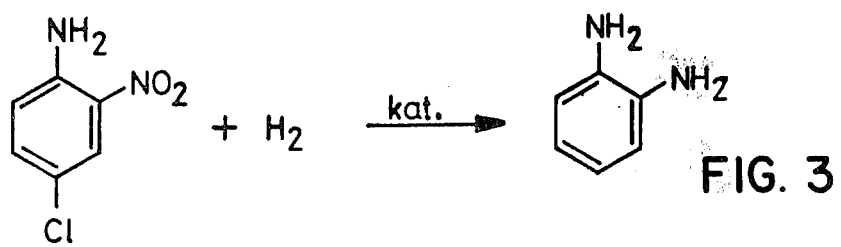

United States Patent [19]

Csikos et al.

[11] 4,207,261

[45] Jun. 10, 1980

[54] PROCESS FOR PREPARING O-PHENYLENEDIAMINE

[75] Inventors: Rezsö Csikos,

[73] Assignee: Magyar Ásványolaj és Földgáz Kisérleti Intézet, Veszprém, Hungary

[21] Appl. No.: 932,930

[22] Filed: Aug. 11, 1978

[30] Foreign Application Priority Data

Aug. 12, 1977 [HU] Hungary .............................. MA 2902

[51] Int. Cl.$^2$ ...................... C07C 85/11; C07C 85/04
[52] U.S. Cl. ...................................... 260/580; 260/581
[58] Field of Search ........................ 260/580, 581, 646

[56] References Cited

U.S. PATENT DOCUMENTS 3,576,876   4/1971   Raper et al. ..................... 260/575

FOREIGN PATENT DOCUMENTS 151828  12/1975  Japan ..................................... 260/580

OTHER PUBLICATIONS

Fierz–David, Blangey: Farbenchemie 104, Springer verl. (1947).
Winnacker–Küchler: Kémiai Technólogia I. 739, Müszaki Könyvkiadó, Budapest (1961).
Augustine, "Catalytic Hydrogenation", pp. 91-93 & 125-129 (1965).
Svishchuk et al, "Chem. AB.", vol. 59, AB. No. 6288a (1963).

*Primary Examiner*—John Doll

[57] ABSTRACT

The invention relates to a process for preparing o-phenylenediamine. According to the invention 1,4-dichlorobenzene is nitrated to give 2,5-dichloro-nitrobenzene which is then reacted with an aqueous ammonium hydroxide solution and the 4-chloro-2-nitraniline obtained is subjected to catalytic hydrogenation to afford the end product which can thereafter be separated.

The process according to the invention can be accomplished with a total yield of about 90% related to the 1,4-dichlorobenzene starting compound.

o-Phenylenediamine is a valuable intermediate for instance in the synthesis of plant protecting agents and heat-resistant polymers.

6 Claims, 1 Drawing Figure

PROCESS FOR PREPARING O-PHENYLENEDIAMINE

This invention relates to a process for preparing o-phenylenediamine. According to the invention 1,4-dichlorobenzene is nitrated to give 2,5-dichloronitrobenzene which is reacted in a second reaction step with an aqueous ammonium hydroxide solution. The 4-chloro-2-nitraniline obtained is then hydrogenated in the presence of a catalyst to afford the desired o-phenylenediamine, which can be separated in a manner known per se.

o-Phenylenediamine is an important intermediate for instance in the manufacture of plant protecting agents and heat-resistance polymers.

According to the processes known in the art o-phenylenediamine is prepared by conventional methods known for the preparation of aromatic amines. Aromatic amines are most frequently obtained by reducing a corresponding nitro compound or by subjecting a corresponding halo derivative to ammonolysis. For example by reducing o-dinitrobenzene o-phenylenediamine can be prepared in a single reaction step (Bull. Soc. Chim. France (4/7, 956). The method cannot be, however, accomplished on an industrial scale since o-dinitrobenzene cannot be prepared by a direct nitration.

On the other hand, although o-dichlorobenzene is a potential starting material for the production of o-phenylenediamine, since it is readily formed by the chlorination of benzene accompanied by a double quantity of p-dichlorobenzene, the ammonolysis resulting in the formation of o-phenylenediamine can be performed even at a high temperature and under an elevated pressure only with a low yield.

From the only prior art publication in which a practical realization of this process is reported it is also apparent that the separation of the copper salt catalyst necessary for the reaction also causes technical difficulties (see German Patent specification No. 654,394).

o-Phenylenediamine can be prepared also starting from o-chloro-nitrobenzene by ammonolysis and a subsequent reduction. o-Chloro-nitrobenzene used as a starting material in this synthesis is prepared from chlorobenzene by nitration when also p-chloro-nitrobenzene is obtained in a triple quantity related to the corresponding o-compound. Consequently an economic production of o-phenylenediamine starting from o-chloro-nitrobenzene necessitates also a simultaneous utilization of p-chloro-nitrobenzene.

It can be seen that the main problem in connection with the known processes is the assurance of the starting material. The ortho-bifunctional derivatives can be obtained from the readily available raw materials, such as benzene, chlorobenzene or nitrobenzene only with a very low yield, after cumbersome separation steps.

In further methods known in the art for the preparation of o-phenylenediamine aniline or an aniline derivative is used as a starting material. When starting from aniline and using ammonia as a reactant the end product is obtained only with a yield of 20 to 25% even when the reaction is carried out at a temperature of 350° C. and under a pressure of 300 to 400 atm. (see DOS No. 2,114,170). Since the direct nitration of aniline does not lead to the desired result, to obtain 0-nitroaniline with an acceptable yield the amino group of aniline should at first be acetylated to acetanilide. Under safe nitrating conditions the o-isomer is accompanied by a considerable quantity of the p-isomer, on the other hand the methods by which substantially only the o-isomer is obtained are explosive.(J. Prakt. Chem. 102 171). o-Nitroaniline can be reduced to o-phenylenediamine in a manner known per se.

By sulphonating acetaniline p-acetamido-benzenesulphonic acid can be prepared which can be converted to 3-nitro-4-acetamino-benzenesulphonic acid by nitration. Desulphonation and hydrolysis of the latter compound affords o-nitroaniline without a substantial quantity of a by-product. o-Nitroaniline can thereafter be reduced to give o-phenylenediamine. A considerable drawback of this multi-step synthesis consists in the formation of waste acid and other by-products in large quantities. This method has been used therefore only for laboratory purposes (Chem. Ber. 58, 2286, 2288/1925).

When chlorinating acetanilide in addition to o-chloro-acetaniline which can be used for the preparation of o-phenylenediamine also about 50% of the corresponding p-isomer are formed (J. Chem. Soc. 95, 1057).

To sum up the characteristics of the known processes the conclusion can be drawn that during the production of compounds suitable for a direct preparation of o-phenylenediamine the desired products are accompanied by large quantities of undesired by-products. To obtain the ortho-isomer with a suitable yield complicated, multistep and occasionally hazardous processes must be employed.

When studying the possibilities for the preparation of o-phenylenediamine we found that o-phenylenediamine can be prepared from 1,4-dichlorobenzene in three reaction steps: nitration, selective ammonolysis and catalytic hydrogenation with a good yield. The process is illustrated by the attached chart.

According to the equation (1) nitration of 1,4-dichlorobenzene results in the formation of 2,5-dichloro-nitrobenzene. 2,5-Dichloro-nitrobenzene can thereafter be reacted with ammonia selectively to give 4-chloro-2-nitraniline as illustrated by equation. (2). Catalytic hydrogenation of 4-chloro-2-nitraniline and a simultaneous dehalogenation affords o-phenylenediamine as shown from the equation (3).

The preparation of o-phenylene diamine according to the reaction route described above until now has not been described in the literature. Moreover, there is neither teaching nor suggestion for the preparation of o-phenylenediamine from 1,4 dichlorobenzene in any other way.

We have surprisingly found that o-phenylenediamine can be prepared from 1,4-dichlorobenzene according to the equations of (1) to (3) with a total yield of about 85 to 90%, without the formation of a considerable amount of by-products. 1,4Dichlorobenzene is a usual product obtained by the chlorination of benzene. This dichloro-compound can be easily isolated, and by a proper conduction of the reaction it can be achieved that this compound is obtained as a main product. In this way the starting material for the process according to the invention can be readily prepared. Due to the chemical character of the starting material and the intermediate prepared therefrom the formation of an isomeric by-product during the preparation of o-phenylenediamine is impossible. In this case consequently there is no need for the separation and utilization of various by-products, the process is independent.

The first, nitrating reaction step can be accomplished in a manner known in the art (Fierz-David, Blangey: Farbenchemie 104, Springer Verl. (1947)). Itis carried out in a concentrated sulphuric acid suspension with a mixed acid, at a temperature of 30 to 40° C., with a yield of 97 to 98%. The product is isolated from the sulphuric acid suspension by dilution with ice water and a subsequent filtration.

A 99% yield was achieved when the nitrating acid was added at a temperature of 35 to 40° C., under an intensive cooling, the nitrating acid was allowed to react until it has entirely been used up and the product was isolated from the sulphuric acid by cooling and a subsequent filtration and finally was washed with water and dried. The waste acid contained in the filtrate can be made use of repeatedly, after supplementation with oleum.

2,5-Dichloro-nitrobenzene can be converted into 4-chloro-2-nitraniline without any purification, according to the equation (2). According to the processes known in the art this reaction can be performed with a 10-fold molar excess of an aqueous or alcoholic ammonia solution, at 170 to 200° C., in more hours.

When a 40 to 50% ammonia solution is employed, over 200° C. the reaction time can be decreased to 35 minutes /Winnacker-Küchler: Kémiai technologia I. 739, Müszaki Könyvkiadó, Budapest (1961)). As a by-product ammonium chloride is formed in this reaction, which can be separated from the main product by washing with water.

When carrying out the process according to the invention a 60 to 90% aqueous ammonium hydroxide solution is used in a 10 to 25-fold excess. Under these conditions a homogenous reaction mixture is obtained, and at the same temperature a considerable shorter reaction time is required to obtain the same yield of 2-nitroaniline than in case of the prior art processes. From the reaction mixture the excess of ammonia is eliminated and 3-chloro-2-nitraniline can be crystallized and the ammonium chloride, formed as a by-product can be separated in the form of a concentrated aqueous solution.

Following the process according to the invention 4-chloro-2-nitroaniline can be transformed into o-phenylenediamine in an aqueous alcoholic solution, in the presence of a hydrogenating catalyst, preferably Raney nickel or palladium on a substrate according to equation (3) by a simultaneous reduction and dehalogenation.

4-Chloro-2-nitraniline is used for hydrogenation in the form of a solution or suspension. As a solvent water-miscible lower alcohols, preferably methanol, ethanol or isopropanol can be used. The preferred catalysts are Raney-nickel or palladium applied to a substrate. Hydrogenation is accomplished at a temperature of 20 to 80° C., preferably 35 to 50° C. and under a pressure of 1 to 20 atm. In order to complete the dehalogenation a basic additive, advantageously an alkali metal hydroxide or ammonium hydroxide is added. Thus the by-product formed during the catalytic hydrogenation is an alkali metal or ammonium chloride and the separation of o-phenylenediamine and the inorganic salt formed can easily be accomplished on the basis of the different physical characteristics. For example on the basis of the differences in water-solubility o-phenylenediamine can be separated by a partial evaporation of the solution and by a subsequent filtration.

The process of the invention is illustrated by the following non-limiting examples.

EXAMPLE 2

588 g. of 1,4-Dichlorobenzene are suspended in 720 g. of a 96% aqueous sulphuric acid solution, then the suspension is nitrated with a mixture of 272 g. of a 96% sulphuric acid and 272 g. of a 100% nitric acid. The mixture is allowed to stand for 1.5 hours, whereupon the precipitated 2,5-dichloro-nitrobenzene is filtered off and washed with water to give 760 g. of 2,5 -dichloro-nitrobenzene. 1200 g of 2,5-dichloro-nitrobenzene are filled into a 7 lit. laboratory shaking autoclave and aminated with a 16-fold molar excess of a 77% aqueous ammonium hydroxide solution at 200 to 220° C. The excess of ammonia is released and thereafter the mixture is cooled and ammonium chloride is separated by an aqueous washing to afford 1062 g. of 4-chloro-2nitraniline in a purity of 98%.

To 87 g. of 4-chloro-2-nitraniline a five-fold amount of ethanol and 50 g. of a Raney-nickel catalyst are added. Reduction and dehalogenation are carried out with hydrogen of 16 atm. at 40 to 50° C., with addition of 100 g. of a 20% solution of sodium hydroxide, in a laboratory autoclave. When no more hydrogen is used up, catalyst is filtered off from the reaction mixture and the filtrate is evaporated until o-phenylenediamine begins to crystallize. In this way 49 g. of o-phenylenediamine are obtained in a purity of 98%.

EXAMPLE 2

0.1 mole of 2,5-dichloro-nitrobenzene prepared according to Example 1 are aminated with a 36-fold molar excess of a 66% aqueous ammonium hydroxide solution at 190° C. 4-chloro-2-nitraniline is obtained with a yield of 96%.

Hydrogenation is accomplished in a laboratory glass equipment equipped with a gas distributor under atmospheric pressure. As a catalyst Raney-nickel is used in a quantity of 40% related to the quantity of 4-chloro-2-nitraniline. 4-chloro-2-nitraniline is added as a 12% methanolic solution. At the same rate, simultaneously an equivalent quantity of a 30% aqueous sodium hydroxide solution is also added into the reaction mixture dropwise. After filtering off the catalyst and evaporating the solution o-phenylenediamine is obtained with a yield of 88%. Catalyst can be repeatedly used up.

EXAMPLE 3

0.1 Moles of 2,5-dichloro-nitrobenzene prepared according to Example 1 are aminated with a 20-fold molar excess of a 86% ammonium hydroxide solution at 160° C. 4-Chloro-2-nitraniline is obtained with a yield of 97%.

Hydrogenation is performed in a laboratory glass equipment described in Example 2, in the presence of 50% of a catalyst calculated for 4-chloro-2-nitraniline. Addition of 4-chloro-2-nitraniline is performed in the form of a 10% isopropanolic solution. As a catalyst a 9% palladium on charcoal catalyst is used. Hydrogenation is carried out under atmospheric pressure and hydrogen is passed through a 25% aqueous ammonium hydroxide solution before entering the equipment. The reaction temperature is 35° C. After filtering off the catalyst the solvent is distilled off from the filtrate until crystallization of o-phenylenediamine is observed. Cooling and filtration afford o-penylenediamine with a yield of 86%. Catalyst can be repeatedly used up.

The main advantages of the process according to the invention are as follows:

(1) 1,4-Dichlorobenzene is used as a starting material which is the main by-product of chlorination of benzene and can be easily separated from the other isomeric by-products. 1,4-Dichlorobenzene is a not very expensive material and by a suitable conduction of the reaction it can be achieved that this compound is formed as a main product.

(2) Nitration of 1,4-dichlorobenzene can practically be accomplished without the formation of by-products, with an excellent yield. The product need not be further purified, and the waste acid formed can be recycled after a suitable supplementation of fresh acid.

(3) By means of a concentrated aqueous ammonium hydroxide solution 2,5-dichloro-nitrobenzene can be converted into 4-chloro-2-nitraniline with a yield of 98%, without the formation of substantial quantities of organic by-products. The use of a concentrated, aqueous ammonium hydroxide solution allows to reduce the reaction time, and the large-scale production according to this method can be accomplished in a simpler apparatus, under a lower pressure. The mechanical stirring, which generally aims at a better contact between the phases, can entirely be omitted.

(4) Reduction of the nitro group of 4-chloro-2-nitraniline and dehalogenation can be performed in a single reaction step. The quantity of the organic by-product is not sufficient.

(5) The total yield of the three-step synthesis is more than 90% related to the 1,4-dichlorobenzene starting material, no special raw materials are required. As a by-product only alkali metal and/or ammonium chlorides are formed in a substantial quantity, but their separation can be easily carried out.

What we claim is:

1. A process for preparing o-phenylenediamine, which comprises nitrating 1,4-dichlorobenzene to give 2,5-dichloronitrobenzene, aminating the latter compound with a 10-36 molar excess of a 60-90% aqueous ammonium hydroxide solution at a temperture of 160° to 220° C., subjecting the 4-chloro-2-nitraniline obtained to catalytic hydrogenation and finally separating the o-phenylenediamine in a manner known per se.

2. A process as claimed in claim 1, which comprises recycling the waste acid formed in a previous nitrating cycle and supplemented by oleum into the nitrating step of 1,4-dichlorobenzene.

3. A process as claimed in claim 1, which comprises carrying out hydrogenation in a water-miscible, monofunctional aliphatic alcohol or aqueous alcohol solution, in the presence of a basic additive and dehydrogenating catalyst, under a pressure of 1 to 20 atm.

4. A process as claimed in claim 3, which comprises using an alkali metal hydroxide and/or ammonium hydroxide as a basic additive.

5. A process as claimed in claim 3, which comprises using active Raney-nickel or a palladium on charcoal catalyst as a hydrogenating catalyst.

6. A process of reacting 2,5-dichloronitrobenzene with a 60-90% aqueous ammonium hydroxide solution at a temperature of 160° to 220° C. to produce 4-chloro-2-nitraniline.

* * * * *